United States Patent
Behr et al.

(10) Patent No.: US 7,193,071 B2
(45) Date of Patent: Mar. 20, 2007

(54) CORN EVENT PV-ZMGT32(NK603) AND COMPOSITIONS AND METHODS FOR DETECTION THEREOF

(75) Inventors: Carl Frederick Behr, Wildwood, MO (US); Gregory R. Heck, Crystal Lake Park, MO (US); Catherine Hironaka Hironaka, Dublin, CA (US); Jinsong You, Ballwin, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 10/790,430

(22) Filed: Mar. 1, 2004

(65) Prior Publication Data

US 2004/0139493 A1    Jul. 15, 2004

(51) Int. Cl.
*C07H 21/02* (2006.01)
*C07H 21/04* (2006.01)
*C12Q 1/68* (2006.01)

(52) U.S. Cl. .............. 536/23.1; 536/24.31; 536/24.33; 435/6

(58) Field of Classification Search ............ 536/24.31, 536/24.33, 23.1, 23.31, 23.33; 435/6
See application file for complete search history.

(56) References Cited

U.S. PATENT DOCUMENTS

| | | | |
|---|---|---|---|
| 5,164,316 A | | 11/1992 | McPherson et al. |
| 5,362,865 A | | 11/1994 | Austin |
| 5,424,412 A | | 6/1995 | Brown et al. |
| 5,641,876 A | * | 6/1997 | McElroy et al. .......... 536/24.1 |
| 5,853,973 A | | 12/1998 | Kakefuda et al. |
| 5,948,956 A | | 9/1999 | Lee et al. |
| 6,040,497 A | | 3/2000 | Spencer et al. |
| 6,448,476 B1 | * | 9/2002 | Barry .................... 800/300 |

FOREIGN PATENT DOCUMENTS

WO    WO 98/44140    10/1998
WO    WO 02/27004    4/2002

OTHER PUBLICATIONS

Sigma Catalog. Molecular biology products-oligonucleotides. p. 1565, 1997.*
Marra et al. The WashU-HHMI mouse EST project. EST, Oct. 29, 1996.*
Strittmatter et al. Cotranscription and processing of 23S, 4.5S and 5S rRNA in chloroplasts from Zea mays. Nucleic Acids Res., vol. 12, No. 20, pp. 7633-7647, 1984.*
Buck et al. Design strategies and performance of custom DNA sequencing primers. Biotechniques, vol. 27, No. 3, pp. 528-536, 1999.*
Cheng et al., Effective amplification of long targets from cloned inserts and human genomic DNA, *Proc. Natl. Acad. Sci. USA* 91:5695-5699 (1994).
Fraley et al., Expression of bacterial genes in plant cells, *Proc.Natl. Acad. Sci. USA* 80:4803-4807 (1983).
Klee et al., Cloning of an *Arabidopsis thaliana* gene encoding 5-enolpyruvylshikimate-3-phosphate synthase: sequence analysis and manipulation to obtain glyphosate-tolerant plants, *Mol. Gen. Genet.* 210:437-442 (1987).
Songstad et al., Production of transgenic maize plants nd progeny by bombardment of HI-II immature embryos, *In Vitro Cell. Dev. Biol.* 32:179-183 (1996).
Windels et al., Development of a line specific GMO detection method: a case study, *Med. Fac. Landbouww, Univ. Gent.* 64:459-462 (1999).

\* cited by examiner

*Primary Examiner*—Suryaprabha Chunduru
(74) *Attorney, Agent, or Firm*—M. Todd Rands; Howrey LLP

(57) ABSTRACT

The present invention provides a DNA construct that confers tolerance to transgenic corn plant. Also provided are assays for detecting the presence of the PV-ZMGT32(nk603) corn event based on the DNA sequence of the recombinant construct inserted into the corn genome and of genomic sequences flanking the insertion site.

6 Claims, 1 Drawing Sheet

CORN EVENT PV-ZMGT32(NK603) AND COMPOSITIONS AND METHODS FOR DETECTION THEREOF

FIELD OF THE INVENTION

The present invention relates to the field of plant molecular biology, specifically the invention relates to a DNA construct for conferring glyphosate tolerance to a plant. The invention more specifically relates to a glyphosate tolerant corn plant PV-ZMGT32(nk603) and to assays for detecting the presence of corn plant PV-ZMGT32(nk603) DNA in a sample and compositions thereof.

BACKGROUND OF THE INVENTION

This invention relates to the glyphosate herbicide tolerant corn (*Zea mays*) plant PV-ZMGT32(nk603) and to the DNA plant expression construct of corn plant PV-ZMGT32 (nk603) and the detection of the transgene/genomic insertion region in corn PV-ZMGT32(nk603) and progeny thereof.

Corn is an important crop and is a primary food source in many areas of the world. The methods of biotechnology have been applied to corn for improvement of the agronomic traits and the quality of the product. One such agronomic trait is herbicide tolerance, in particular, tolerance to glyphosate herbicide. This trait in corn has been conferred by the expression of a transgene in the corn plants (U.S. Pat. No. 6,040,497).

The expression of foreign genes in plants is known to be influenced by their chromosomal position, perhaps due to chromatin structure (e.g., heterochromatin) or the proximity of transcriptional regulation elements (e.g., enhancers) close to the integration site (Weising et al., Ann. Rev. Genet 22:421–477, 1988). For this reason, it is often necessary to screen a large number of events in order to identify an event characterized by optimal expression of a introduced gene of interest. For example, it has been observed in plants and in other organisms that there may be a wide variation in levels of expression of an introduced genes among events. There may also be differences in spatial or temporal patterns of expression, for example, differences in the relative expression of a transgene in various plant tissues, that may not correspond to the patterns expected from transcriptional regulatory elements present in the introduced gene construct. For this reason, it is common to produce hundreds to thousands of different events and screen those events for a single event that has desired transgene expression levels and patterns for commercial purposes. An event that has desired levels or patterns of transgene expression is useful for introgressing the transgene into other genetic backgrounds by sexual outcrossing using conventional breeding methods. Progeny of such crosses maintain the transgene expression characteristics of the original transformant. This strategy is used to ensure reliable gene expression in a number of varieties that are well adapted to local growing conditions.

It would be advantageous to be able to detect the presence of a particular event in order to determine whether progeny of a sexual cross contain a transgene of interest. In addition, a method for detecting a particular event would be helpful for complying with regulations requiring the premarket approval and labeling of foods derived from recombinant crop plants, for example. It is possible to detect the presence of a transgene by any well known nucleic acid detection method such as the polymerase chain reaction (PCR) or DNA hybridization using nucleic acid probes. These detection methods generally focus on frequently used genetic elements, such as promoters, terminators, marker genes, etc. As a result, such methods may not be useful for discriminating between different events, particularly those produced using the same DNA construct unless the DNA sequence of chromosomal DNA adjacent to the inserted DNA ("flanking DNA") is known. An event-specific PCR assay is discussed, for example, by Windels et al. (Med. Fac. Landbouww, Univ. Gent 64/5b:459–462, 1999), who identified glyphosate tolerant soybean event 40-3-2 by PCR using a primer set spanning the junction between the insert and flanking DNA, specifically one primer that included sequence from the insert and a second primer that included sequence from flanking DNA.

SUMMARY OF THE INVENTION

According to one aspect of the invention, a DNA construct is provided that when expressed in plant cells and plants confers tolerance to glyphosate herbicide. This invention relates preferably to the methods for producing and selecting a glyphosate tolerant monocot crop plant. The DNA construct consists of two transgene expression cassettes. The first expression cassette comprising a DNA molecule of a rice (*Oryzae sativa*) actin 1 promoter and rice actin 1 intron operably joined to a DNA molecule encoding a chloroplast transit peptide sequence, operably connected to a DNA molecule encoding a glyphosate resistant 5-enol-pyruvylshikimate-3-phosphate synthase (EPSPS), operably connected to a DNA molecule comprising a 3' transcriptional terminator. The second transgene expression cassette of the DNA construct comprising a DNA molecule of the cauliflower mosaic virus (CaMV) 35S promoter, operably connected to a DNA molecule comprising a Hsp70 intron, operably connected to a DNA molecule encoding a chloroplast transit peptide sequence, operably connected to a DNA molecule encoding a glyphosate resistant 5-enol-pyruvylshikimate-3-phosphate synthase (EPSPS), operably connected to a DNA molecule comprising a 3' transcriptional terminator.

More specifically, a DNA construct is provided that when expressed in plant cells and plants confers tolerance to glyphosate herbicide. This invention relates preferably to the methods for producing and selecting a glyphosate tolerant corn plant. The DNA construct consists of two transgene expression cassettes. The first expression cassette consisting of a DNA molecule of a rice (*Oryzae sativa*) actin 1 promoter and rice actin 1 intron operably joined to a DNA molecule encoding an *Arabidopsis* EPSPS chloroplast transit peptide sequence, operably connected to a DNA molecule encoding a glyphosate resistant 5-enol-pyruvylshikimate-3-phosphate synthase (EPSPS) isolated from *Agrobacterium tumefaciens* sp. strain CP4, operably connected to a DNA molecule consisting of a nopaline synthase transcriptional terminator. The second transgene expression cassette consisting of a DNA molecule of the cauliflower mosaic virus (CaMV) 35S promoter containing a tandem duplication of the enhancer region, operably connected to a DNA molecule consisting of a *Zea mays* Hsp70 intron, operably connected to a DNA molecule encoding an *Arabidopsis* EPSPS chloroplast transit peptide sequence, operably connected to a DNA molecule encoding a glyphosate resistant 5-enol-pyruvylshikimate-3-phosphate synthase (EPSPS) isolated from *Agrobacterium tumefaciens* sp. strain CP4, operably connected to a DNA molecule consisting of a nopaline synthase transcriptional terminator.

According to another aspect of the invention, compositions and methods are provided for detecting the presence of the transgene/genomic insertion region from a novel corn plant designated PV-ZMGT32(nk603). DNA molecules are provided that comprise at least one junction sequence of PV-ZMGT32(nk603) selected from the group consisting of 5' TGTAGCGGCCCACGCGTGGT 3' (SEQ ID NO:9), 5' TACCACGCGACACACTTC 3' (SEQ ID NO:10), and 5' TGCTGTTCTGCTGACTTT 3' (SEQ ID NO:11) and complements thereof; wherein a junction sequence spans the junction between heterologous DNA inserted into the genome and the DNA from the corn cell flanking the insertion site and is diagnostic for the event. The corn plant and seed comprising these molecules is an aspect of this invention.

A novel DNA molecule 5'ACCAAGCTTTTATAATAG 3' (SEQ ID NO:12) and the complement thereof, wherein this DNA molecule is novel in PV-ZMGT32(nk603) and its progeny. The corn plant and seed comprising this molecule is an aspect of this invention.

According to another aspect of the invention, DNA molecules that comprise the novel transgene/genomic insertion region, SEQ ID NO:7 and SEQ ID NO:8 and are homologous or complementary to SEQ ID NO:7 and SEQ ID NO:8 are an aspect of this invention.

DNA molecules that comprise a sufficient length of a transgene portion of the DNA sequence of SEQ ID NO:7 and a similar sufficient length of a 5' flanking corn DNA sequence of SEQ ID NO:7; or a similar sufficient length of a transgene portion of the DNA sequence of SEQ ID NO:8 and a similar sufficient length of a 3' DNA sequence flanking the transgene, wherein these DNA molecules are useful as DNA primers in DNA amplification methods so as to provide a DNA amplicon product specifically produced from PV-ZMGT32(nk603) DNA and its progeny are another aspect of the invention. DNA primers homologous or complementary to a length of SEQ ID NO:7 and SEQ ID NO:8 are an aspect of the invention. The amplicons produced using DNA primers that are diagnostic for corn event PV-ZMGT32(nk603) and its progeny are a subject of this invention.

According to another aspect of the invention, methods of detecting the presence of DNA corresponding to the corn event PV-ZMGT32(nk603) event in a sample are provided. Such methods comprise: (a) contacting the sample comprising DNA with a DNA primer set, that when used in a nucleic acid amplification reaction with genomic DNA extracted from corn event PV-ZMGT32 (nk603) produces an amplicon that is diagnostic for corn event PV-ZMGT32(nk603); (b) performing a nucleic acid amplification reaction, thereby producing the amplicon; and (c) detecting the amplicon. A pair of DNA molecules comprising a DNA primer set that are homologous or complementary to SEQ ID NO:7 or SEQ ID NO:8 that function in a nucleic acid amplification reaction to produce an amplicon DNA molecule diagnostic for PV-ZMGT329nk603). More specifically, a pair of DNA molecules comprising a DNA primer set, wherein the DNA molecules are identified as SEQ ID NO:13 or complements thereof and SEQ ID NO:14 or complements thereof; SEQ ID NO:15 or complements thereof and SEQ ID NO:16 or complements thereof. The amplicon comprising the DNA molecules of SEQ ID NO:13 and SEQ ID NO:14. The amplicon comprising the DNA molecules of SEQ ID NO:15 and SEQ ID NO:16. The amplicon produce by the afore described method that can hybridize under stringent conditions to SEQ ID NO:9, SEQ ID NO:10, SEQ ID NO:11, or SEQ ID NO:12.

According to another aspect of the invention, methods of detecting the presence of a DNA molecule corresponding to the PV-ZMGT32(nk603) event in a sample, such methods comprising: (a) contacting the sample comprising DNA extracted from a corn plant with a DNA probe molecule that hybridizes under stringent hybridization conditions with genomic DNA from corn event PV-ZMGT32(nk603) and does not hybridize under the stringent hybridization conditions with a control corn plant DNA; (b) subjecting the sample and probe to stringent hybridization conditions; and (c) detecting hybridization of the probe to the DNA. More specifically, a method for detecting the presence of a DNA molecule corresponding to the PV-ZMGT32(nk603) event in a sample, such methods, consisting of (a) contacting the sample comprising DNA extracted from a corn plant with a DNA probe molecule that consists of SEQ ID NO:9, SEQ ID NO:10, SEQ ID NO:11, or SEQ ID NO:12, wherein said DNA probe molecule hybridizes under stringent hybridization conditions with genomic DNA from corn event PV-ZMGT32(nk603) and does not hybridize under the stringent hybridization conditions with a control corn plant DNA; (b) subjecting the sample and probe to stringent hybridization conditions; and (c) detecting hybridization of the probe to the DNA.

According to another aspect of the invention, methods of producing a corn plant that tolerates application of glyphosate are provided that comprise the steps of: (a) sexually crossing a first parental corn line comprising the expression cassettes of the present invention, which confers tolerance to application of glyphosate, and a second parental corn line that lacks the glyphosate tolerance, thereby producing a plurality of progeny plants; and (b) selecting a progeny plant that tolerates application of glyphosate. Such methods may optionally comprise the further step of back-crossing the progeny plant to the second parental corn line to producing a true-breeding corn plant that tolerates application of glyphosate.

According to another aspect of the invention, a method is provided to select for glyphosate tolerant corn plants of the present invention and progeny thereof comprising extracting DNA from a plant sample, contacting a DNA with a marker nucleic acid molecule selected from the group consisting of SEQ ID NO:9, SEQ ID NO:10, SEQ ID NO:11, or SEQ ID NO:12, or complements thereof, detecting the hybridization of said marker nucleic acid molecule to the DNA, and performing a marker assisted breeding analysis for the genetic linkage of the glyphosate tolerant trait to the marker nucleic acid molecule.

The present invention provides a method of producing a corn plant tolerant to glyphosate herbicide comprising transforming a corn cell with the DNA construct (pMON25496), selecting the corn cell for tolerance to the treatment with an effective dose of glyphosate, and growing the corn cell into a fertile corn plant. The fertile corn plant can be self pollinated or crossed with compatible corn varieties to produce glyphosate tolerant progeny.

The invention further relates to a DNA detection kit comprising at least one DNA molecule of sufficient length of contiguous nucleotides homologous or complementary to SEQ ID NO:7 or SEQ ID NO:8 that functions as a DNA primer or probe specific for corn event PV-ZMGT32(nk603) or its progeny.

This invention further relates to the plants and seeds of glyphosate tolerant corn (*Zea mays*) PV-ZMGT32 (nk603) having ATCC Accession No. PTA-2478 and the progeny derived thereof. The corn plant or its parts produced by growing of the glyphosate tolerant corn plant PV-ZMGT32 (nk603), the pollen and ovules of the corn plant PV-ZMGT32(nk603). The nuclei of vegetative cells, the nuclei of pollen cells, and the nuclei of egg cells of the corn plant PV-ZMGT32 (nk603) and the progeny derived thereof. The corn plant and seed PV-ZMGT32(nk603) from which the DNA primer molecules of the present invention provide a specific amplicon product is an aspect of the invention.

The foregoing and other aspects of the invention will become more apparent from the following detailed description and accompanying drawings.

DETAILED DESCRIPTION OF THE PREFERRED EMBODIMENTS

Figure 1:
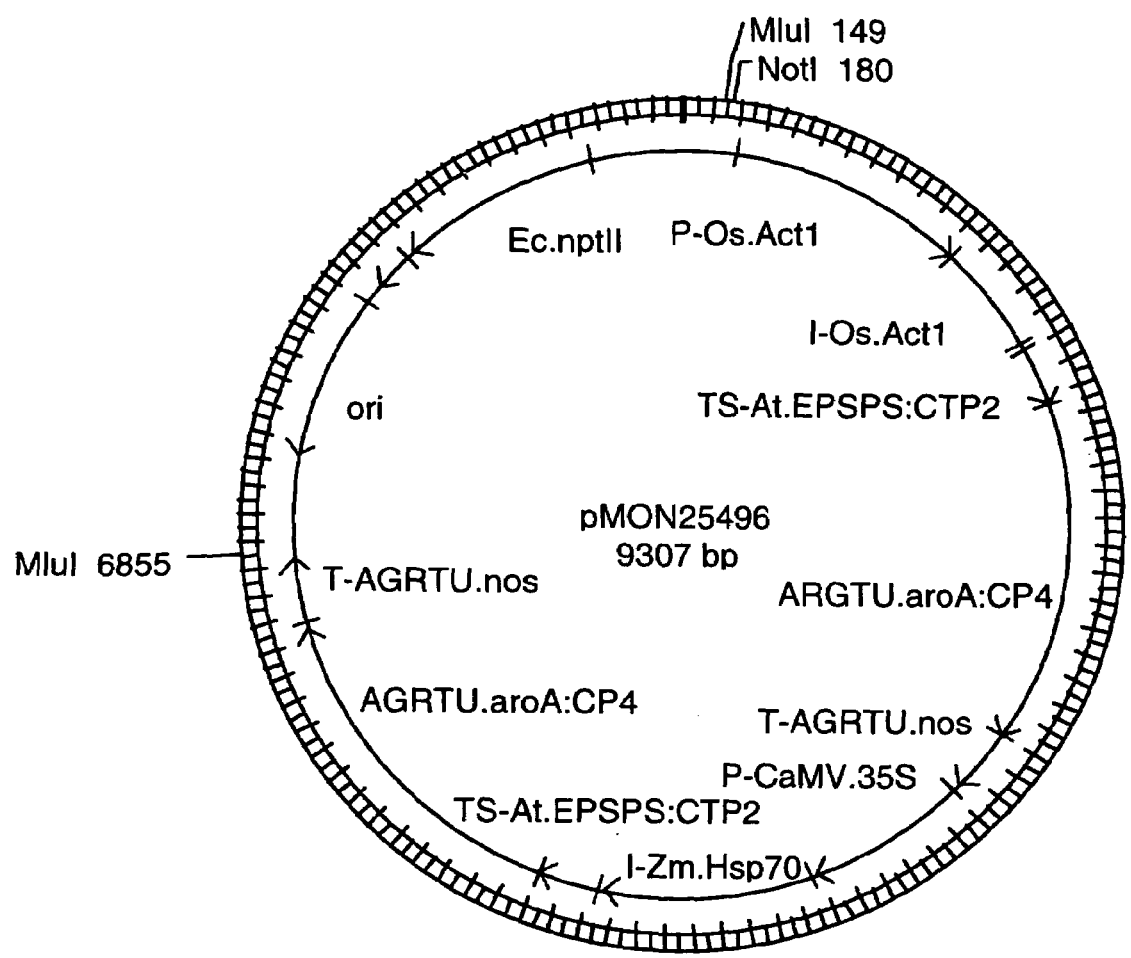
FIG. 1. Plasmid map of pMON25496

This application claims the benefit of U.S. Provisional Application No.60/213,567, filed Jun. 22, 2000; U.S. Provisional Application No. 60/241,215, filed Oct. 13, 2000; and U.S. Provisional Application No. 60/240,014, filed Oct. 13, 2000. The following definitions and methods are provided to better define the present invention and to guide those of ordinary skill in the art in the practice of the present invention. Unless otherwise noted, terms are to be understood according to conventional usage by those of ordinary skill in the relevant art. Definitions of common terms in molecular biology may also be found in Rieger et al., *Glossary of Genetics: Classical and Molecular*, 5th edition, Springer-Verlag: New York, 1991; and Lewin, *Genes V*, Oxford University Press: New York, 1994. The nomenclature for DNA bases as set forth at 37 CFR §1.822 is used.

As used herein, the term "corn" means *Zea mays* or maize and includes all plant varieties that can be bred with corn, including wild maize species.

As used herein, the term "comprising" means "including but not limited to". "Glyphosate" refers to N-phosphonomethylglycine and its salts, Glyphosate is the active ingredient of Roundup® herbicide (Monsanto Co.). Treatments with "glyphosate herbicide" refer to treatments with the Roundup®, Roundup Ultra®, Roundup UltraMax® herbicide or any other herbicide formulation containing glyphosate. The selection of application rates for a glyphosate formulation that constitute a biologically effective dose is within the skill of the ordinary agricultural technician.

A DNA construct is an assembly of DNA molecules linked together that provide one or more expression cassettes. The DNA construct is preferably a plasmid that is enabled for self replication in a bacterial cell and contains various endonuclease enzyme restriction sites that are useful for introducing DNA molecules that provide functional genetic elements, i.e., promoters, introns, leaders, coding sequences, 3' termination regions, among others. The expression cassettes contained within a DNA construct comprise the necessary genetic elements to provide transcription of a messenger RNA. The expression cassettes can be designed to express in prokaryote cells or eukaryotic cells. The expression cassettes of the present invention are designed to express most preferably in plant cells.

A transgenic "event" is produced by transformation of plant cells with heterologous DNA construct, including a nucleic acid expression cassette that comprises a transgene of interest, the regeneration of a population of plants resulting from the insertion of the transgene into the genome of the plant, and selection of a particular plant characterized by insertion into a particular genome location. The term "event" refers to the original transformant and progeny of the transformant that include the heterologous DNA. The term "event" also refers to progeny produced by a sexual outcross between the transformant and another variety that include the heterologous DNA. Even after repeated back-crossing to a recurrent parent, the inserted DNA and flanking DNA from the transformed parent is present in the progeny of the cross at the same chromosomal location. The term "event" also refers to DNA from the original transformant comprising the inserted DNA and flanking genomic sequence immediately adjacent to the inserted DNA that would be expected to be transferred to a progeny that receives inserted DNA including the transgene of interest as the result of a sexual cross of one parental line that includes the inserted DNA (e.g., the original transformant and progeny resulting from selfing) and a parental line that does not contain the inserted DNA. A glyphosate tolerant corn plant PV-ZMGT32 (nk603) can be breed by first sexually crossing a first parental corn plant consisting of a corn plant grown from the transgenic corn plant PV-ZMGT32 (nk603) having ATCC Accession No. PTA-2478 and progeny thereof derived from transformation with the expression cassettes of the present invention that tolerates application of glyphosate herbicide, and a second parental corn plant that lacks the tolerance to glyphosate herbicide, thereby producing a plurality of first progeny plants; and then selecting a first progeny plant that is tolerant to application of glyphosate herbicide; and selfing the first progeny plant, thereby producing a plurality of second progeny plants; and then selecting from the second progeny plants a glyphosate herbicide tolerant plant. These steps can further include the back-crossing of the first glyphosate tolerant progeny plant or the second glyphosate tolerant progeny plant to the second parental corn plant or a third parental corn plant, thereby producing a corn plant that tolerates the application of glyphosate herbicide.

It is also to be understood that two different transgenic plants can also be mated to produce offspring that contain two independently segregating added, exogenous genes. Selfing of appropriate progeny can produce plants that are homozygous for both added, exogenous genes. Back-crossing to a parental plant and out-crossing with a non-transgenic plant are also contemplated, as is vegetative propagation. Descriptions of other breeding methods that are commonly used for different traits and crops can be found in one of several references, e.g., Fehr, in *Breeding Methods for Cultivar Development*, Wilcox J. ed., American Society of Agronomy, Madison Wis. (1987).

A "probe" is an isolated nucleic acid to which is attached a conventional detectable label or reporter molecule, e.g., a radioactive isotope, ligand, chemiluminescent agent, or enzyme. Such a probe is complementary to a strand of a target nucleic acid, in the case of the present invention, to a strand of genomic DNA from corn event PV-ZMGT32 (nk603) whether from a corn plant or from a sample that includes DNA from the event. Probes according to the present invention include not only deoxyribonucleic or ribonucleic acids but also polyamides and other probe materials that bind specifically to a target DNA sequence and can be used to detect the presence of that target DNA sequence.

"Primers" are isolated nucleic acids that are annealed to a complementary target DNA strand by nucleic acid hybridization to form a hybrid between the primer and the target DNA strand, then extended along the target DNA strand by a polymerase, e.g., a DNA polymerase. Primer pairs of the present invention refer to their use for amplification of a target nucleic acid sequence, e.g., by the polymerase chain reaction (PCR) or other conventional nucleic-acid amplification methods.

Probes and primers are of sufficient nucleotide length to bind to the target DNA sequence specifically in the hybridization conditions or reaction conditions determined by the operator. This length may be of any length that is of sufficient length to be useful in the detection method of choice. Generally, 11 nucleotides or more in length, preferably 18 nucleotides or more, more preferably 24 nucleotides or more, and most preferably 30 nucleotides or more are used. Such probes and primers hybridize specifically to a target sequence under high stringency hybridization conditions. Preferably, probes and primers according to the present invention have complete DNA sequence similarity of contiguous nucleotides with the target sequence, although probes differing from the target DNA sequence and that retain the ability to hybridize to target DNA sequences may be designed by conventional methods.

Methods for preparing and using probes and primers are described, for example, in *Molecular Cloning: A Laboratory Manual*, 2nd ed., vol. 1–3, ed. Sambrook et al., Cold Spring Harbor Laboratory Press, Cold Spring Harbor, N.Y., 1989 (hereinafter, "Sambrook et al., 1989"); *Current Protocols in Molecular Biology*, ed. Ausubel et al., Greene Publishing and Wiley-Interscience, New York, 1992 (with periodic updates) (hereinafter, "Ausubel et al., 1992"); and Innis et al., *PCR Protocols: A Guide to Methods and Applications*, Academic Press: San Diego, 1990. PCR-primer pairs can be derived from a known sequence, for example, by using computer programs intended for that purpose such as Primer (Version 0.5, © 1991, Whitehead Institute for Biomedical Research, Cambridge, Mass.).

Primers and probes based on the flanking DNA and insert sequences disclosed herein can be used to confirm (and, if necessary, to correct) the disclosed sequences by conventional methods, e.g., by re-cloning and sequencing such sequences.

The nucleic acid probes and primers of the present invention hybridize under stringent conditions to a target DNA sequence. Any conventional nucleic acid hybridization or amplification method can be used to identify the presence of DNA from a transgenic event in a sample. Nucleic acid molecules or fragments thereof are capable of specifically hybridizing to other nucleic acid molecules under certain circumstances. As used herein, two nucleic acid molecules are said to be capable of specifically hybridizing to one another if the two molecules are capable of forming an anti-parallel, double-stranded nucleic acid structure. A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described by Sambrook et al., 1989, and by Haymes et al., In: *Nucleic Acid Hybridization, A Practical Approach*, IRL Press, Washington, D.C. (1985), Departures from complete complementarity are therefore permissible, as long as such departures do not completely preclude the capacity of the molecules to form a double-stranded structure. In order for a nucleic acid molecule to serve as a primer or probe it need only be sufficiently complementary in sequence to be able to form a stable double-stranded structure under the particular solvent and salt concentrations employed.

As used herein, a substantially homologous sequence is a nucleic acid molecule that will specifically hybridize to the complement of the nucleic acid molecule to which it is being compared under high stringency conditions. Appropriate stringency conditions which promote DNA hybridization, for example, 6.0× sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989), 6.3.1–6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed. In a preferred embodiment, a nucleic acid of the present invention will specifically hybridize to one or more of the nucleic acid molecules set forth in SEQ ID NO: 9, 10, 11 and 12 or complements thereof or fragments of either under moderately stringent conditions, for example at about 2.0×SSC an about 65° C. In a particularly preferred embodiment, a nucleic acid of the present invention will specifically hybridize to one or more of the nucleic acid molecules set forth in SEQ ID NO:9 through SEQ ID NO:12 or complements or fragments of either under high stringency conditions. In one aspect of the present invention, a preferred marker nucleic acid molecule of the present invention has the nucleic acid sequence set forth in SEQ ID NO:9 through SEQ ID NO:12 or complements thereof or fragments of either. In another aspect of the present invention, a preferred marker nucleic acid molecule of the present invention shares between 80% and 100% or 90% and 100% sequence identity with the nucleic acid sequence set forth in SEQ ID NO:9 through SEQ ID NO:12 or complement thereof or fragments of either. In a further aspect of the present invention, a preferred marker nucleic acid molecule of the present invention shares between 95% and 100% sequence identity with the sequence set forth in SEQ ID NO:9 through SEQ ID NO:12 or complement thereof or fragments of either. SEQ ID NO:9 through SEQ IN NO:12 may be used as markers in plant breeding methods to identify the progeny of genetic crosses similar to the methods described for simple sequence repeat DNA marker analysis, in "DNA markers: Protocols, applications, and overviews: (1997) 173–185, Cregan, et al., eds., Wiley-Liss NY; all of which is herein incorporated by reference in its' entirely. The hybridization of the probe to the target DNA molecule can be detected by any number of methods known to those skilled in the art, these can include, but are not limited to, fluorescent tags, radioactive tags, antibody based tags, and chemiluminescent tags.

Regarding the amplification of a target nucleic acid sequence (e.g., by PCR) using a particular amplification primer pair, "stringent conditions" are conditions that permit the primer pair to hybridize only to the target nucleic-acid sequence to which a primer having the corresponding wild-type sequence (or its complement) would bind and preferably to produce a unique amplification product, the amplicon, in a DNA thermal amplification reaction.

The term "specific for (a target sequence)" indicates that a probe or primer hybridizes under stringent hybridization conditions only to the target sequence in a sample comprising the target sequence.

As used herein, "amplified DNA" or "amplicon" refers to the product of nucleic-acid amplification of a target nucleic acid sequence that is part of a nucleic acid template. For example, to determine whether the corn plant resulting from a sexual cross contains transgenic event genomic DNA from the corn plant of the present invention, DNA extracted from a corn plant tissue sample may be subjected to nucleic acid amplification method using a DNA primer pair that includes a first primer derived from flanking sequence in the genome of the plant adjacent to the insertion site of inserted heterologous DNA, and a second primer derived from the inserted heterologous DNA to produce an amplicon that is diagnostic for the presence of the event DNA. The amplicon is of a length and has a sequence that is also diagnostic for the event. The amplicon may range in length from the combined length of the primer pairs plus one nucleotide base pair, preferably plus about fifty nucleotide base pairs, more preferably plus about two hundred-fifty nucleotide base pairs, and even more preferably plus about four hundred-fifty nucleotide base pairs. Alternatively, a primer pair can be derived from flanking sequence on both sides of the inserted DNA so as to produce an amplicon that includes the entire insert nucleotide sequence (e.g., the MluI DNA fragment of the pMON25496 expression construct, FIG. 1, approximately 6706 nucleotide base pairs). A member of a primer pair derived from the plant genomic sequence may be located a distance from the inserted DNA sequence, this distance can range from one nucleotide base pair up to the limits of the amplification reaction, or about twenty thousand nucleotide base pairs. The use of the term "amplicon" specifically excludes primer dimers that may be formed in the DNA thermal amplification reaction.

Nucleic-acid amplification can be accomplished by any of the various nucleic-acid amplification methods known in the art, including the polymerase chain reaction (PCR). A variety of amplification methods are known in the art and are described, inter alia, in U.S. Pat. Nos. 4,683,195 and 4,683,202 and in PCR Protocols: A Guide to Methods and Applications, ed. Innis et al., Academic Press, San Diego, 1990. PCR amplification methods have been developed to amplify up to 22 kb of genomic DNA and up to 42 kb of bacteriophage DNA (Cheng et al., Proc. Natl. Acad. Sci. USA 91:5695–5699, 1994). These methods as well as other methods known in the art of DNA amplification may be used in the practice of the present invention. The sequence of the heterologous DNA insert or flanking DNA sequence from corn event PV-ZMGT32(nk603) can be verified (and corrected if necessary) by amplifying such sequences from DNA extracted from the ATCC deposit Accession No. PTA-2478 seed or plants using DNA primers derived from the sequences provided herein followed by standard DNA sequencing of the PCR amplicon or of the cloned DNA.

The amplicon produced by these methods may be detected by a plurality of techniques. One such method is Genetic Bit Analysis (Nikiforov, et al. Nucleic Acid Res. 22:4167–4175, 1994) where an DNA oligonucleotide is designed which overlaps both the adjacent flanking genomic DNA sequence and the inserted DNA sequence. The oligonucleotide is immobilized in wells of a microwell plate. Following PCR of the region of interest (using one primer in the inserted sequence and one in the adjacent flanking genomic sequence), a single-stranded PCR product can be hybridized to the immobilized oligonucleotide and serve as a template for a single base extension reaction using a DNA polymerase and labelled ddNTPs specific for the expected next base. Readout may be fluorescent or ELISA-based. A signal indicates presence of the insert/flanking sequence due to successful amplification, hybridization, and single base extension.

Another method is the Pyrosequencing technique as described by Winge (Innov. Pharma. Tech. 00:18–24, 2000). In this method an oligonucleotide is designed that overlaps the adjacent genomic DNA and insert DNA junction. The oligonucleotide is hybridized to single-stranded PCR product from the region of interest (one primer in the inserted sequence and one in the flanking genomic sequence) and incubated in the presence of a DNA polymerase, ATP, sulfurylase, luciferase, apyrase, adenosine 5' phosphosulfate and luciferin. DNTPs are added individually and the incorporation results in a light signal which is measured. A light signal indicates the presence of the transgene insert/flanking sequence due to successful amplification, hybridization, and single or multi-base extension.

Fluorescence Polarization as described by Chen, et al., (Genome Res. 9:492–498, 1999) is a method that can be used to detect the amplicon of the present invention. Using this method an oligonucleotide is designed which overlaps the genomic flanking and inserted DNA junction. The oligonucleotide is hybridized to single-stranded PCR product from the region of interest (one primer in the inserted DNA and one in the flanking genomic DNA sequence) and incubated in the presence of a DNA polymerase and a fluorescent-labeled ddNTP. Single base extension results in incorporation of the ddNTP. Incorporation can be measured as a change in polarization using a fluorometer. A change in polarization indicates the presence of the transgene insert/flanking sequence due to successful amplification, hybridization, and single base extension.

Taqman® (PE Applied Biosystems, Foster City, Calif.) is described as a method of detecting and quantifying the presence of a DNA sequence and is fully understood in the instructions provided by the manufacturer. Briefly, a FRET oligonucleotide probe is designed which overlaps the genomic flanking and insert DNA junction. The FRET probe and PCR primers (one primer in the insert DNA sequence and one in the flanking genomic sequence) are cycled in the presence of a thermostable polymerase and dNTPs. Hybridization of the FRET probe results in cleavage and release of the fluorescent moiety away from the quenching moiety on the FRET probe. A fluorescent signal indicates the presence of the flanking/transgene insert sequence due to successful amplification and hybridization.

Molecular Beacons have been described for use in sequence detection as described in Tyangi, et al. (Nature Biotech. 14:303–308, 1996) Briefly, a FRET oligonucleotide probe is designed that overlaps the flanking genomic and insert DNA junction. The unique structure of the FRET probe results in it containing secondary structure that keeps the fluorescent and quenching moieties in close proximity. The FRET probe and PCR primers (one primer in the insert DNA sequence and one in the flanking genomic sequence) are cycled in the presence of a thermostable polymerase and dNTPs. Following successful PCR amplification, hybridization of the FRET probe to the target sequence results in the removal of the probe secondary structure and spatial separation of the fluorescent and quenching moieties. A fluorescent signal results. A fluorescent signal indicates the presence of the flanking/transgene insert sequence due to successful amplification and hybridization.

The following examples are included to demonstrate examples of certain preferred embodiments of the invention. It should be appreciated by those of skill in the art that the techniques disclosed in the examples that follow represent approaches the inventors have found function well in the practice of the invention, and thus can be considered to constitute examples of preferred modes for its practice. However, those of skill in the art should, in light of the present disclosure, appreciate that many changes can be made in the specific embodiments that are disclosed and still obtain a like or similar result without departing from the spirit and scope of the invention.

EXAMPLES

Example 1

The PV-ZMGT32(nk603) (hence forth referred to as nk603) transgenic corn event was generated by microprojectile bombardment of maize embryos (Songstad et al., In Vitro Cell Plant 32:179–183, 1996) using a linear Mlu I DNA fragment derived from pMON25496 (FIG. 1). This DNA fragment contains two transgene expression cassettes that collectively confer corn plant tolerance to glyphosate. The first cassette is composed of the rice actin 1 promoter and intron (P-Os.Act1 and I-Os.Act1, U.S. Pat. No. 5,641,876), operably connected to an *Arabidopsis* EPSPS chloroplast transit peptide (TS-At.EPSPS:CTP2, Klee et al., Mol. Gen. Genet. 210:47–442, 1987), operably connected to a glyphosate tolerant 5-enol-pyruvylshikimate-3-phosphate synthase (EPSPS) from *Agrobacterium* sp. strain CP4 (AGRTU.aroA:CP4, U.S. Pat. No. 5,633,435) and operably connected to a nopaline synthase transcriptional terminator (T-AGRTU.nos, Fraley et al. Proc. Natl. Acad. Sci. USA 80:4803–4807, 1983). The second transgene expression cassette consists of the cauliflower mosaic virus 35S promoter containing a tandem duplication of the enhancer region (P-CaMV.35S, Kay et al. Science 236:1299–1302, 1987; U.S. Pat. No. 5,164,316), operably connected to a *Zea mays* Hsp70 intron (I-Zm.Hsp70, U.S. Pat. No. 5,362,865), operably connected to an *Arabidopsis* EPSPS chloroplast transit peptide (TS-At.EPSPS:CTP2, Klee et al., Mol. Gen. Genet. 210:47–442, 1987), operably connected to a glyphosate tolerant 5-enol-pyruvylshikimate-3-phosphate synthase (EPSPS) from *Agrobacterium* sp. strain CP4 (AGRTU.aroA: CP4, U.S. Pat. No. 5,633,435) and operably connected to a nopaline synthase transcriptional terminator (T-AGRTU.nos, Fraley et al. Proc. Natl. Acad. Sci. USA 80:4803–4807, 1983). Post-bombardment, glyphosate-tolerant transgenic calli were selected on media containing 3 mM glyphosate and plants were subsequently regenerated. Three hundred-four plants from 91 independent transgenic events were produced, nk603 was selected from this population based on a superior combination of characteristics, including glyphosate tolerance, agronomic performance, and single transgenic insertion. Greenhouse and field evaluations of the nk603 event and its derived progeny indicated this transgenic insertion confers tolerance that exceeds commercial specifications for full vegetative and reproductive tolerance to 340 g glyphosate/acre (840 g glyphosate/hectare; 32 oz Roundup Ultra/acre) when applied at the V4 and V8 leaf stages.

Example 2

The glyphosate tolerant nk603 corn event was compared to the current commercial standard, GA21 (U.S. Pat. No. 6,040,497), for tolerance to glyphosate vegetative injury and effect on yield. GA21 contains at least 3 transgene expression cassettes arranged in tandem in the genome of GA21 event (SCP/GMO/232-Final, European Commission Health & Consumer Protection Directorate-General). The transgene cassette of GA21 consists of a rice actin 1 promoter and intron linked to a ribulose 1,5-bisphosphate carboxylase chloroplast transit peptide linked to a modified maize glyphosate resistant EPSPS and a 3' nopaline synthase transcription termination region. Plants of nk603 and GA21 were planted in rows in replicated field plots. The treatments were 1) unsprayed, 2) sprayed at a 64 ounces/acre rate of Roundup Ultra® at V4 leaf stage and again with 64 ounces/acre Roundup Ultra® at V8 leaf stage, 3) sprayed at a 96 ounces/acre rate of Roundup Ultra® at V4 leaf stage and again with 96 ounces/acre Roundup Ultra® at V8 leaf stage. Vegetative tolerance was measured as percent vegetative injury determined by the amount of leaf malformation observed 10 days after the herbicide treatment at the V8 leaf stage. The yield of each plot was measured in bushels/acre and the percent reduction in yield determined for each herbicide treatment relative to the unsprayed treatment. The results shown in Table 1 illustrates that nk603 shows a lower percent vegetative injury level than the GA21 plants and the observed percent yield reduction is also less for the nk603 event. A low incidence of vegetative injury was observed in the unsprayed plots, this observation is attributable to various environmental factors other than glyphosate herbicide exposure. The double expression cassette of pMON25496 in nk603 was compared to vegetative injury and fertility rating of 3 independent corn events obtained from only the CaMV.35S promoter driving expression of the glyphosate tolerance gene (AGRTU.aroA:CP4). It was observed that the double expression cassette conferred a higher level of vegetative tolerance and reproductive tolerance than three independent corn events (ev 1, ev 2, and ev 3) containing only the expression cassette where the glyphosate tolerance gene expression was driven by the CaMV.35S promoter. A higher level of vegetative tolerance to glyphosate herbicide injury was observed for nk603 plus 3 additional corn events derived from pMON25496 when compared to the average injury of 6 corn events derived from a construct where the glyphosate tolerance gene expression was driven only by the rice actin promoter and intron (P-Os.Act1/I-Os.Act1). The plants transformed with the double expression cassette possessed a higher level of glyphosate tolerance to vegetative and fertility injury than plants derived from transformation with the single expression cassettes this resulted in improved resistance to yield loss due to glyphosate herbicide application. The pMON25496 construct provides two plant expression cassettes at a single location in nk603 that confers a higher lever of glyphosate tolerance than the triple tandem insertion occurring in the commercial standard, GA21.

TABLE 1

Glyphosate Tolerance of nk603 - Vegetative injury, Yield, and Fertility Rating

| Event | Treatment | % Veg injury* | Yield (bushels/acre) | % Yield red. |
|---|---|---|---|---|
| GA21 | Unsprayed | 0.3 | 142.2 | |
| | 64 oz Roundup Ultra ® at V4 followed by 64 oz at V8 | 5.3 | 134.1 | 5.7 |
| | 96 oz Roundup Ultra ® at V4 followed by 96 oz at V8 | 8.3 | 129.1 | 9.2 |

TABLE 1-continued

Glyphosate Tolerance of nk603 - Vegetative injury, Yield, and Fertility Rating

| nk603 | | | | |
|---|---|---|---|---|
| | Unsprayed | 0.9 | 145.6 | |
| | 64 oz Roundup Ultra ® at V4 followed by 64 oz at V8 | 2.9 | 138.5 | 4.9 |
| | 96 oz Roundup Ultra ® at V4 followed by 96 oz at V8 | 4.7 | 140.1 | 3.8 |

| | Treatment | Fertility Rating** |
|---|---|---|
| nk603 | 64 oz Roundup ® Ultra at V8 | 4.5 |
| CaMV.35S ev 1 | 64 oz Roundup ® Ultra at V8 | 2.0 |
| CaMV.35S ev 2 | 64 oz Roundup ® Ultra at V8 | 2.2 |
| CaMV.35S ev 3 | 64 oz Roundup ® Ultra at V8 | 2.4 |

| | Treatment | ave. % Veg injury* |
|---|---|---|
| nk603 plus 3 additional pMON25496 events | 128 oz Roundup ® Ultra at V4 followed by 128 oz at V8 | 22.9 |
| Six P-Os.Act1 single cassette events | 128 oz Roundup ® Ultra at V4 followed by 128 oz at V8 | 28.9 |

*Veg injury is observed 10 days after V8 treatment is one measure taken to assess vegetative injury in response to glyphosate treatment.
**Male fertility rating: 4–5 = fully fertile; 3 = significantly reduced pollen shed; 0–2 = completely sterile - highly sterile, not suitable for commercial use.

Example 3

The corresponding flanking DNA molecule from nk603 was cloned by using ligated adapters and nested PCR as described in the Genome Walker™ kit (catalog #K1807-1, CloneTech Laboratories, Inc, Palo Alto, Calif.). First, genomic DNA from the nk603 event was purified by the CTAB purification method (Rogers et al., Plant Mol. Biol. 5:69–76, 1985). The genomic DNA libraries for amplification were prepared according to manufacturer's instructions (Genome Walker™, CloneTech Laboratories, Inc, Palo Alto, Calif.). In separate reactions, genomic DNA was digested overnight at 37° C. with the following blunt-end restriction endonucleases: EcoRV, ScaI, DraI, PvuII, and StuI (CloneTech Laboratories, Inc, Palo Alto, Calif.). The reaction mixtures were extracted with phenol:chloroform, the DNA was precipitated by the addition of ethanol to the aqueous phase, pelleted by centrifugation, then resuspended in Tris-EDTA buffer (10 mM Tris-.HCl, pH 8.0, 1 mM EDTA). The purified blunt-ended genomic DNA fragments were ligated to the Genome Walker™ adapters according to the manufacturer's protocol. After ligation, each reaction was heat treated (70° C. for 5 min) to terminate the reaction and then diluted 10-fold in Tris-EDTA buffer. One µl of each respective ligation was then amplified in a 50 µl reaction that included 1 µl of respective adapter-ligated library, 1 µl of 10 µM Genome Walker™ adapter primer AP1 (5'GTATATC-GACTCACTATAGGGC 3', SEQ ID NO:1), 1 µl of 10 µM nk603 transgene-specific oligonucleotide (5' TGACGTAT-CAAAGTACCGACAAAAACATCC 3' SEQ ID NO:2), 1 µl 10 mM deoxyribonucleotides, 2.5 µl dimethyl sulfoxide, 5 µl of 10× PCR buffer containing MgCl$_2$, 0.5 µl (2.5 units)of Amplitaq thermostable DNA polymerase (PE AppliedBiosystems, Foster City, Calif.), and H$_2$O to 50 µl. The reactions were performed in a thermocycler using calculated temperature control and the following cycling conditions: 1 cycle of 95° C. for 9 min; 7 cycles of 94° C. for 2 s, 70° C. for 3 min; 36 cycles of 94° C. for 2 s, 65° C. for 3 min; 1 cycle of 65° C. for 4 min. One µl of each primary reaction was diluted 50-fold with water and amplified in a secondary reaction (1 µl of respective diluted primary reaction, 1 µl of 10 µM Genome Walker™ nested adapter primer AP2 (5'ACTAT-AGGGCACGCGTGGT 3', SEQ ID NO:3, supplied by manufacturer), 1 µl of 10 µM nk603 transgene-specific nested oligonucleotide (5' CTTTGTTTTATTTTGGAC-TATCCCGACTC 3', SEQ ID NO:4), 1 µl 10 mM deoxyribonucleotides, 2.5 µl dimethyl sulfoxide, 5 µl of 10× PCR buffer containing MgCl$_2$, 0.5 µl (2.5 units)of Amplitaq thermostable DNA polymerase (PE Applied Biosystems, Foster City, Calif.), and H$_2$O to 50 µl] using the following cycling conditions: 1 cycle of 95° C. for 9 min; 5 cycles of 94° C. for 2 s, 70° C. for 3 min; 24 cycles of 94° C. for 2 s, 65° C. for 3 min; 1 cycle of 65° C. for 4 min.

PCR products, representing 5' regions that span the junction between the nk603 transgenic insertion and the neighboring flanking corn DNA were purified by agarose gel electrophoresis followed by purification from the agarose matrix using the QIAquick Gel Extraction Kit (catalog #28704, Qiagen Inc., Valencia, Calif.) and direct cloning into the pGEM-T Easy vector (catalog. #A1360, Promega, Madison, Wis.). The identity of the cloned PCR products and relationship to the Mlu I fragment of pMON25496 was confirmed by DNA sequence analysis (ABI Prism™ 377, PE Biosystems, Foster City, Calif. and DNASTAR sequence analysis software, DNASTAR Inc., Madison, Wis.).

Similarly, the nk603 3' flanking corn DNA sequence was amplified and cloned using nested gene specific primers, such as, SEQ ID NO:5 (5' AGATTGAATCCTGTTGCCG-GTCTTGC 3') and SEQ ID NO:6 (5' GCGGTGTCATC-TATGTTACTAGATCGGG 3') that anneal to the T-AGR-TU.nos transcriptional terminator. Two T-AGRTU.nos transcriptional terminators are present in the nk603 transgenic/genomic insertion, one internal in the construct and one at the 3' end of the construct adjacent to corn genomic DNA. The PCR products produced in this reaction were sequenced and the DNA sequence that spans the junction between transgene and flanking sequence was distinguished from products of the internal T-AGRTU.nos by comparison to the known genetic element sequences of the pMON25496 construct as previously described.

Corn DNA sequence flanking both sides of the transgenic insertion was determined for nk603 by sequencing the Genome Walker™-derived amplification products and alignment to known transgene sequence. At the 5' end of the transgenic insertion, the sequence of a 498 bp segment around the insertion junction was determined (SEQ ID NO:7). This consisted of 304 base pairs (bp) of the flanking maize genomic DNA sequence (nucleotides 1-304 of SEQ ID NO:7), 45 bp of pMON25496 construct DNA sequence (nucleotides 305–349 of SEQ ID NO:7) and 149 bp of DNA sequence from the 5' end of P-Os.Act1 (nucleotides 350–498 of SEQ ID NO:7).

The DNA sequence was determined for a 1183 bp segment around the 3' insertion junction (SEQ ID NO:8), that begins with 164 bp of the T-AGRTU.nos transcriptional terminator (nucleotides 1–164 of SEQ ID NO:8), 217 bp of pMON25496 construct DNA sequence (nucleotides 165–381 of SEQ ID NO:8), 305 bp of the maize plastid genes, rpsll and rpoA (partial segments of each gene corresponding to bases 63–363 of Genbank accession X07810, corresponding to bases 382–686 of SEQ ID NO:8), and the remaining DNA sequence consisting of maize genomic DNA sequence flanking the integration site (corresponding to bases 687–1183 of SEQ ID NO:8).

The junction DNA molecules, SEQ ID NO:9, 10, 11, and 12 are novel DNA molecules in nk603 and are diagnostic for corn plant nk603 and its progeny. The junction molecules in SEQ ID NO:9, 10, and 11 represent about 9 nucleotides on each side of an insertion site of a transgene DNA fragment and corn genomic DNA. SEQ ID NO:9 is found at nucleotide positions 295–314 of SEQ ID NO:7. The junction sequences SEQ ID NO:10 and 11 are located at nucleotide positions 373–390 and 678–695, respectively, of SEQ ID NO:8, representing a junction DNA molecule of construct DNA sequence with corn plastid DNA sequence (SEQ ID NO:10) and construct sequence with corn genomic DNA sequence (SEQ ID NO:11). SEQ ID NO:12 is located at nucleotide position 156–173 of SEQ ID NO:8 and represents a novel DNA molecule in nk603 due to it being a fusion of the T-AGRTU.nos terminator sequence with an inverted fragment of the rice actin promoter DNA sequence.

Example 4

DNA event primer pairs are used to produce an amplicon diagnostic for nk603. These event primer pairs include but are not limited to SEQ ID NO:13 and SEQ ID NO:14 for the 5' amplicon DNA molecule and SEQ ID NO:15 and SEQ ID NO:16 for the 3' amplicon DNA molecule. In addition to these primer pairs, any primer pair derived from SEQ ID NO:7 and SEQ ID NO:8 that when used in a DNA amplification reaction produces a DNA amplicon diagnostic for nk603 is an aspect of the present invention. The amplification conditions for this analysis is illustrated in Table 2 and Table 3 for the 5' transgene insert/genomic junction region. The same method is applied for amplification of the 3' amplicon DNA molecule using primer DNA molecules SEQ ID NO:15 and SEQ ID NO:16, however, any modification of these methods that use DNA molecules or complements thereof to produce an amplicon DNA molecule diagnostic for nk603 is within the ordinary skill of the art. In addition, a control primer pair (SEQ ID NO:17 and 18) for amplification of an endogenous corn gene is included as an internal standard for the reaction conditions. The analysis of nk603 plant tissue DNA extract sample should include a positive tissue DNA extract control from nk603, a negative DNA extract control from a corn plant that is not nk603, and a negative control that contains no template corn DNA extract. Additional DNA primer molecules of sufficient length can be selected from SEQ ID NO:7 and SEQ ID NO:8 by those skilled in the art of DNA amplification methods, and conditions optimized for the production of an amplicon that may differ from the methods shown in Table 2 and Table 3 but result in an amplicon diagnostic for nk603. The use of these DNA primer sequences with modifications to the methods of Table 2 and 3 are within the scope of the invention. The amplicon wherein at least one DNA primer molecule of sufficient length derived from SEQ ID NO:7 and SEQ ID NO:8 that is diagnostic for nk603 is an aspect of the invention. The amplicon wherein at least one DNA primer of sufficient length derived from any of the genetic elements of pMON25496 that is diagnostic for nk603 is an aspect of the invention. The assay for the nk603 amplicon can be performed by using a Stratagene Robocycler, MJ Engine, Perkin-Elmer 9700, or Eppendorf Mastercycler Gradient thermocycler as shown in Table 3, or by methods and apparatus known to those skilled in the art.

TABLE 2

PCR procedure and reaction mixture for the confirmation of nk603 5' transgene insert/genomic junction region.

| Step | Reagent | Amount | Comments |
|---|---|---|---|
| 1 | Nuclease-free water | add to final volume of 20 μl | — |
| 2 | 10 × reaction buffer (with MgCl$_2$) | 2.0 μl | 1 × final concentration of buffer, 1.5 mM final concentration of MgCl$_2$ |
| 3 | 10 mM solution of dATP, dCTP, dGTP, and dTTP | 0.4 μl | 200 μM final concentration of each dNTP |
| 4 | event primer (SEQ ID NO: 13) (resuspended in 1 × TE buffer or nuclease-free water to a concentration of 10 μM) | 0.4 μl | 0.2 μM final concentration |
| 5 | event primer (SEQ ID NO: 14) (resuspended in 1 × TE buffer or nuclease-free water to a concentration of 10 μM) | 0.4 μl | 0.2 μM final concentration |
| 6 | control primer (SEQ ID NO: 17) (resuspended in 1 × TE buffer or nuclease-free water to a concentration of 10 μM) | 0.2 μl | 0.1 μM final concentration |
| 7 | control primer (SEQ ID NO: 18) (resuspended in 1 × TE buffer or nuclease-free water to a concentration of 10 μM) | 0.2 μl | 0.1 μM final concentration |
| 8 | RNase, DNase free (500 ng/μl) | 0.1 μl | 50 ng/reaction |
| 9 | REDTaq DNA polymerase (1 unit/μl) | 1.0 μl (recommended to switch pipets prior to next step) | 1 unit/reaction |
| 10 | Extracted DNA (template): Samples to be analyzed individual leaves pooled leaves (maximum of 50 leaves/pool) Negative control | 10–200 ng of genomic DNA 200 ng of genomic DNA 50 ng of corn genomic DNA (notnk603) | — |
|  | Negative control | no template DNA |  |
|  | Positive control | 50 ng of nk603 genomic DNA |  |

TABLE 3

Suggested PCR parameters for different thermocyclers
Gently mix and, if needed (no hot top on thermocycler),
add 1–2 drops of mineral oil on top of each reaction.
Proceed with the PCR in a Stratagene Robocycler, MJ
Engine, Perkin-Elmer 9700, or Eppendorf Mastercycler
Gradient thermocycler using the following cycling parameters.

| Cycle No. | Settings: Stratagene Robocycler |
|---|---|
| 1 | 94° C. 3 minutes |
| 38 | 94° C. 1 minute |
|  | 63° C. 1 minute |
|  | 72° C. 1 minute and 30 seconds |
| 1 | 72° C. 10 minutes |

| Cycle No. | Settings: MJ Engine or Perkin-Elmer 9700 |
|---|---|
| 1 | 94° C. 3 minutes |
| 38 | 94° C. 10 seconds |
|  | 63° C. 30 seconds |
|  | 72° C. 1 minute |
| 1 | 72° C. 10 minutes |

| Cycle No. | Settings: Eppendorf Mastercycler Gradient |
|---|---|
| 1 | 94° C. 3 minutes |
| 38 | 94° C. 15 seconds |
|  | 63° C. 15 seconds |
|  | 72° C. 1 minute |
| 1 | 72° C. 10 minutes |

Note:
The MJ Engine or Eppendorf Mastercycler Gradient thermocycler should be run in the calculated mode. Run the Perkin-Elmer 9700 thermocycler with the ramp speed set at maximum.

A deposit of the Monsanto Company, corn seed of event PV-ZMGT32(nk603) disclosed above has been made under the Budapest Treaty with the American Type Culture Collection (ATCC), 10801 University Boulevard, Manassas, Va. 20110. The ATCC accession number is PTA-2478. The deposit will be maintained in the depository for a period of 30 years, or 5 years after the last request, or for the effective life of the patent, whichever is longer, and will be replaced as necessary during that period.

Having illustrated and described the principles of the present invention, it should be apparent to persons skilled in the art that the invention can be modified in arrangement and detail without departing from such principles. We claim all modifications that are within the spirit and scope of the appended claims.

All publications and published patent documents cited in this specification are incorporated herein by reference to the same extent as if each individual publication or patent application was specifically and individually indicated to be incorporated by reference.

We claim:

1. A pair of DNA molecules comprising: a first DNA molecule and a second DNA molecule selected from an insertion junction sequence comprising a maize genomic flanking DNA sequence and an insert DNA sequence, wherein the DNA molecules are at least 11 nucleotides in length, and wherein the first DNA molecule is selected from the maize genomic flanking DNA sequence consisting of contiguous nucleotides 1–304 of SEQ ID NO:7 or its full complement and the second DNA molecule is selected from the insert DNA sequence consisting of contiguous nucleotides 305–498 of SEQ ID NO:7 or its full complement to function as DNA primers or probes diagnostic for DNA extracted from corn plant PV-ZMGT32(nk603) or progeny thereof, wherein said pair of DNA molecules produce an amplicon of SEQ ID NO:9.

2. An artificial DNA molecule comprising the nucleotide sequence selected from the group consisting of SEQ ID NO:9, SEQ ID NO:10, and SEQ ID NO:12, and full complements thereof.

3. A DNA detection kit for corn event PV-ZMGT32 (nk603) and its progeny comprising: at least one DNA molecule of sufficient length of contiguous nucleotides, said DNA molecule being homologous or complementary to nucleotides 1–324 of SEQ ID NO:7 or nucleotides 365–1183 of SEQ ID NO:8.

4. The pair of DNA molecules in claim 1, wherein the DNA molecules are at least 18 nucleotides in length.

5. The pair of DNA molecules in claim 4, wherein the DNA molecules are at least 24 nucleotides in length.

6. The pair of DNA molecules in claim 5, wherein the DNA molecules are at least 30 nucleotides in length.

* * * * *

UNITED STATES PATENT AND TRADEMARK OFFICE
CERTIFICATE OF CORRECTION

PATENT NO. : 7,193,071 B2
APPLICATION NO. : 10/790430
DATED : March 20, 2007
INVENTOR(S) : Carl Frederick Behr et al.

It is certified that error appears in the above-identified patent and that said Letters Patent is hereby corrected as shown below:

Title page item (75), "Catherine Hironaka Hironaka, Dublin, CA" should read:

-- Catherine Hironaka, Dublin CA --

Title page item (60), "Related U.S. Application Data" should be added which reads as follows:

-- divisional of 09/872,051 (filed on June 1, 2001), which claims benefit of 60/213,567 (filed on June 22, 2000) and claims benefit of 60/240,014 (filed on October 13, 2000) and claims benefit of 60/241,215 (filed on October 13, 2000) --

Signed and Sealed this

Twenty-fourth Day of July, 2007

JON W. DUDAS
*Director of the United States Patent and Trademark Office*

SEQUENCE LISTING

<160> NUMBER OF SEQ ID NOS: 16

<210> SEQ ID NO 1
<211> LENGTH: 22
<212> TYPE: DNA
<213> ORGANISM: Artificial Sequence
<220> FEATURE:
<221> NAME/KEY: source
<222> LOCATION: (1)..(22)
<223> OTHER INFORMATION: fully synthesized

<400> SEQUENCE: 1
gtatatcgac tcactatagg gc                                           22

<210> SEQ ID NO 2
<211> LENGTH: 30
<212> TYPE: DNA
<213> ORGANISM: Artificial Sequence
<220> FEATURE:
<221> NAME/KEY: source
<222> LOCATION: (1)..(30)
<223> OTHER INFORMATION: full synthesized

<400> SEQUENCE: 2
tgacgtatca aagtaccgac aaaaacatcc                                   30

<210> SEQ ID NO 3

```
<211> LENGTH: 19
<212> TYPE: DNA
<213> ORGANISM: Artificial Sequence
<220> FEATURE:
<221> NAME/KEY: source
<222> LOCATION: (1)..(19)
<223> OTHER INFORMATION: fully synthesized

<400> SEQUENCE: 3
actatagggc acgcgtggt                                              19

<210> SEQ ID NO 4
<211> LENGTH: 29
<212> TYPE: DNA
<213> ORGANISM: Artificial Sequence
<220> FEATURE:
<221> NAME/KEY: source
<222> LOCATION: (1)..(29)
<223> OTHER INFORMATION: fully synthesized

<400> SEQUENCE: 4
ctttgtttta ttttggacta tcccgactc                                   29

<210> SEQ ID NO 5
<211> LENGTH: 26
<212> TYPE: DNA
<213> ORGANISM: Artificial Sequence
<220> FEATURE:
<221> NAME/KEY: source
<222> LOCATION: (1)..(26)
<223> OTHER INFORMATION: fully synthesized

<400> SEQUENCE: 5
agattgaatc ctgttgccgg tcttgc                                      26

<210> SEQ ID NO 6
<211> LENGTH: 28
<212> TYPE: DNA
<213> ORGANISM: Artificial Sequence
<220> FEATURE:
<221> NAME/KEY: source
<222> LOCATION: (1)..(28)
<223> OTHER INFORMATION: fully synthesized

<400> SEQUENCE: 6
gcggtgtcat ctatgttact agatcggg                                    28

<210> SEQ ID NO 7
<211> LENGTH: 498
<212> TYPE: DNA
<213> ORGANISM: Artificial Sequence
<220> FEATURE:
<221> NAME/KEY: source
<222> LOCATION: (1)..(498)
<223> OTHER INFORMATION: 1-304 Zea maize genomic DNA
                        305-349 construct vector DNA
                        350-498 rice actin 1 promoter DNA

<400> SEQUENCE: 7
aatcgatcca aaatcgcgac tgaaatggtg gaagaaagag agaacagaga gcctcacgtt    60
tccagggtga agtatcagag gatttaccgc ccatgccttt tatggagaca agaaggggag   120
gaggtaaaca gatcagcatc agcgctcgaa agtttcgtca aggatgcgg aactgtttcc    180 agccgccgtc gccattcggc cagactcctc ctctctcggc atgagccgat cttttctctg   240
gcatttccaa ccctagagac gtgcgtccct ggtgggctgc tcggccagca agccttgtag   300
cggcccacgc gtggtaccaa gcttgatatc cctagggcgg ccgcgttaac aagcttactc   360
```

```
gaggtcattc atatgcttga aagagagtc gggatagtcc aaaataaaac aaaggtaaga    420
ttaccggtca aaagtgaaaa catcagttaa aaggtgtata aagtaaaata tcggtaataa    480
aaggtggccc aaagtgaa                                                  498
```

<210> SEQ ID NO 8
<211> LENGTH: 1183
<212> TYPE: DNA
<213> ORGANISM: Artificial Sequence
<220> FEATURE:
<221> NAME/KEY: source
<222> LOCATION: (1)..(1183)
<223> OTHER INFORMATION: 1-164 Agrobacterium tumefaciens nos 3'
    terminator 165-381 construct vector DNA
    382-686 Zea maize plastid genes, rps11 and
    rpoA 687-1183 Zea maize genomic DNA

<400> SEQUENCE: 8

```
gacgttattt atgagatggg tttttatgat tagagtcccg caattataca tttaatacgc     60
gatagaaaac aaaatatagc gcgcaaacta ggataaatta tcgcgcgcgg tgtcatctat    120
gttactagat cggggatatc cccgggggaat tcggtaccaa gcttttataa tagtagaaaa    180
gagtaaattt cactttgggc cacctttat taccgatatt ttactttata ccacctttta    240
actgatgttt tcacttttga ccaggtaatc ttaccttttgt tttattttgg actatcccga    300
ctctcttctc aagcatatga atgacctcga gtaagcttgt taacgcggcc gccctaggga    360
tatcaagctt ggtaccacgc gacacacttc cactctagtg tttgagtgga tcctgttatc    420
tcttctcgaa ccataacaga ctagtattat ttgatcattg aatcgtttat ttctcttgaa    480
agcggtttca ttttttttta cagacgtctt tttttaggag gtcgacatcc attatgcggc    540
ataggtgtta catcgcgtat acaacttaac cgtacaccac ttttagcaat ggctcgtaat    600
gcggcatctc ttccgctacc agcaccttttt accataactt ctgctcgttg caaacccact    660
gtacgaatag catctactgc tgttctgctg actttatttt ttttaataaa gtgaaaaacc    720
ataaaatgga caacaacacc ctgcccttca ctaccggtcg gagcgacgcc gaagatgggg    780
ttcaacacgg tcgcgacacg gatgcaacgg accctccaag ccaatactcg aggccggacc    840
gacgacgtag gcaggggtgg ccataacgac ggtggcggca tccaacttgt tctttcccctt    900 tctctgtctt caacttgcgc cggcagtctg ctagacccag gggatgctgt gtggaggaga    960
ggtcgcgggg cccgattttt atagcctggg cgaggacgag cttggccgaa ccgatccaga   1020
gctctgcgca aatcacgaag aaccagtggg gccgctcgcg cctagcccac cgccaggagc   1080
ggggcttgtt gcgagccgta gcgtcgggaa ggggacgacc cgctaggggg gcccatgctc   1140
cagcgcccag agagaaaaaa agaaaggaag gcgcgagatg atg                     1183
```

<210> SEQ ID NO 9
<211> LENGTH: 19
<212> TYPE: DNA
<213> ORGANISM: Artificial Sequence
<220> FEATURE:
<221> NAME/KEY: source
<222> LOCATION: (1)..(19)
<223> OTHER INFORMATION: Zea maize genomic and vector DNA

<400> SEQUENCE: 9

```
tgtagcggcc cacgcgtgg                                                  19
```

<210> SEQ ID NO 10
<211> LENGTH: 18

```
<212> TYPE: DNA
<213> ORGANISM: Artificial Sequence
<220> FEATURE:
<221> NAME/KEY: source
<222> LOCATION: (1)..(18)
<223> OTHER INFORMATION: zea maize plastid DNA and vector DNA

<400> SEQUENCE: 10
taccacgcga cacacttc                                                  18

<210> SEQ ID NO 11
<211> LENGTH: 18
<212> TYPE: DNA
<213> ORGANISM: Artificial Sequence
<220> FEATURE:
<221> NAME/KEY: source
<222> LOCATION: (1)..(18)
<223> OTHER INFORMATION: Zea maize genomic DNA and vector DNA

<400> SEQUENCE: 11
tgctgttctg ctgacttt                                                  18

<210> SEQ ID NO 12
<211> LENGTH: 18
<212> TYPE: DNA
<213> ORGANISM: Artificial Sequence
<220> FEATURE:
<221> NAME/KEY: source
<222> LOCATION: (1)..(18)
<223> OTHER INFORMATION: Agrobacterium tumefaciens nos 3' terminator and
      rice actin promoter DN

<400> SEQUENCE: 12
accaagcttt tataatag                                                  18

<210> SEQ ID NO 13
<211> LENGTH: 22
<212> TYPE: DNA
<213> ORGANISM: Artificial Sequence
<220> FEATURE:
<221> NAME/KEY: source
<222> LOCATION: (1)..(22)
<223> OTHER INFORMATION: fully synthesized

<400> SEQUENCE: 13
aatcgatcca aaatcgcgac tg                                             22

<210> SEQ ID NO 14
<211> LENGTH: 22
<212> TYPE: DNA
<213> ORGANISM: Artificial Sequence
<220> FEATURE:
<221> NAME/KEY: source
<222> LOCATION: (1)..(22)
<223> OTHER INFORMATION: fully synthesized

<400> SEQUENCE: 14
ttcactttgg gccacctttt at                                             22

<210> SEQ ID NO 15
<211> LENGTH: 22
<212> TYPE: DNA
<213> ORGANISM: Artificial Sequence
<220> FEATURE:
<221> NAME/KEY: source
<222> LOCATION: (1)..(22)
<223> OTHER INFORMATION: fully synthesized

<400> SEQUENCE: 15
```

```
gacgttattt atgagatggg tt                                                    22

<210> SEQ ID NO 16
<211> LENGTH: 22
<212> TYPE: DNA
<213> ORGANISM: Artificial Sequence
<220> FEATURE:
<221> NAME/KEY: source
<222> LOCATION: (1)..(22)
<223> OTHER INFORMATION: fully synthesized

<400> SEQUENCE: 16
catcatctcg cgccttcctt tc                                                    22
```